United States Patent
Beck et al.

(10) Patent No.: US 9,341,168 B2
(45) Date of Patent: May 17, 2016

(54) DEVICE FOR APPLYING A DIRECTED CONTACT PRESSURE FORCE TO A MULTITUDE OF SAMPLES

(71) Applicant: BUNDESREPUBLIK DEUTSCHLAND, VERTRETEN DURCH DAS BUNDESMINISTERIUM FUER WIRTSCHAFT UND TECHNOLOGIE, DIESES VERTRETEN DURCH DEN PRAESIDENTEN DER BAM, BUNDESANSTALT FUER MATERIALFORSCHUNG UND-PRUEFUNG

(72) Inventors: Uwe Beck, Falkensee (DE); Stefan Hielscher, Berlin (DE); Matthias Weise, Berlin (DE); Kai Kittler, Berlin (DE)

(73) Assignee: Bundesrepublik Deutschland, vertreten durch das Bundesministerium für Wirtschaft und Technologie, dieses vertreten durch den Präsidenten der BAM, Bundesanstalt für Materialforschung und—prüfung, Berlin (DE)

( * ) Notice: Subject to any disclaimer, the term of this patent is extended or adjusted under 35 U.S.C. 154(b) by 29 days.

(21) Appl. No.: 13/911,843

(22) Filed: Jun. 6, 2013

(65) Prior Publication Data
US 2013/0327210 A1    Dec. 12, 2013

(30) Foreign Application Priority Data

Jun. 6, 2012 (DE) .................. 10 2012 104 925
Feb. 13, 2013 (DE) .................. 10 2013 101 434
May 21, 2013 (DE) .................. 10 2013 105 150

(51) Int. Cl.
| | |
|---|---|
| B30B 1/32 | (2006.01) |
| F04B 1/00 | (2006.01) |
| G01N 3/08 | (2006.01) |
| G01N 19/04 | (2006.01) |

(Continued)

(52) U.S. Cl.
CPC ... F04B 1/00 (2013.01); B30B 1/32 (2013.01); G01N 3/08 (2013.01); G01N 19/04 (2013.01)

(58) Field of Classification Search
CPC ...................................... B30B 9/3092
USPC ................. 100/208, 251; 156/309.6, 251
See application file for complete search history.

(56) References Cited

U.S. PATENT DOCUMENTS

| | | | | |
|---|---|---|---|---|
| 3,947,204 | A * | 3/1976 | Ayres et al. | 425/383 |
| 5,606,910 | A * | 3/1997 | Katz | 100/208 |
| 7,707,895 | B2 | 5/2010 | Beck et al. | |
| 2004/0079167 | A1 | 4/2004 | Boyko et al. | |
| 2006/0138641 | A1 | 6/2006 | Suzuki | |
| 2011/0132209 | A1 * | 6/2011 | Senda et al. | 100/35 |

FOREIGN PATENT DOCUMENTS

GB    2196437    4/1988

* cited by examiner

Primary Examiner — Scott W Dodds
(74) Attorney, Agent, or Firm — Dicke, Billig & Czaja, PLLC

(57) ABSTRACT

A device for applying a directed contact pressure force to a multitude of samples. A first part of the device includes a multitude of sample receptacles that receive a multitude of joining surface modules of the same kind, and a second part of the device is connected to the first part in such a manner that a multitude of fluidically intercommunicating hydraulic cylinders in one of the two parts can load the joining surface modules simultaneously in a loading direction at a predetermined force that is substantially identical in respect to all samples.

14 Claims, 12 Drawing Sheets

DEVICE FOR APPLYING A DIRECTED CONTACT PRESSURE FORCE TO A MULTITUDE OF SAMPLES

CROSS-REFERENCE TO RELATED APPLICATIONS

This Utility Patent Application claims priority to German Patent Application No. 10 2012 104 925.4, filed Jun. 6, 2012, Germany Patent Application No. 10 2013 101 434.8, filed Feb. 13, 2013 and German Patent Application No. 10 2013 105 150.2, filed May 21, 2013, all of which are incorporated herein by reference.

BACKGROUND

The invention relates to the field of joining, in one embodiment of integrally joining, and concerns a device for simultaneously subjecting a multitude of samples to identical pressure irrespective of the height of the samples.

SUMMARY

For assessing the suitability of adhesives or solders for particular material combinations or for assessing surface treatment processes that are preceded by bonding processes or soldering processes, usually a test stamp is bonded or soldered to the respective substrate, and following curing of the adhesive or following re-melting of a solder deposit the strength of the achieved integrally joined bond is examined at defined tensile loading or shear loading.

Since on the one hand the thickness of different substrates, and on the other hand also the thickness of an applied adhesive layer or of a solder deposit can vary, e.g., depending on the viscosity, the size of particles or fillers contained in the adhesive or in a soldering paste, the resulting height of different layer structures with otherwise standardised test stamps is subject to certain variations in addition to normal specimen variability.

Now, if simultaneously several substrates, including layers, coatings or composites, and the test stamps destined for the aforesaid are to be bonded, soldered or otherwise integrally connected, it may be necessary to hold a multitude of stacks, including a substrate, an adhesive layer or a solder deposit and a test stamp, prior to the actual bonding or soldering, for a particular dwell time at a defined pressure. If this were to take place by using a weight, for example a metal plate, placed simultaneously and collectively onto all the stacks, the respectively resulting pressure would not be uniform. Thus, with the above-mentioned variations in the sample height of different joined connections the comparability of the test results relating to strength would not be ensured.

Known solutions that are based on the use of contact pressure springs are only usable to a limited extend for the designated purpose because the effective spring constant of different springs can vary due to manufacturing tolerances even in the case of identical spring geometry, and furthermore the spring constant applies only to a narrow deflection range. Thus the respectively exerted spring force typically deviates from the nominal value outside a predetermined tolerance range.

For these and other reasons there is a need for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
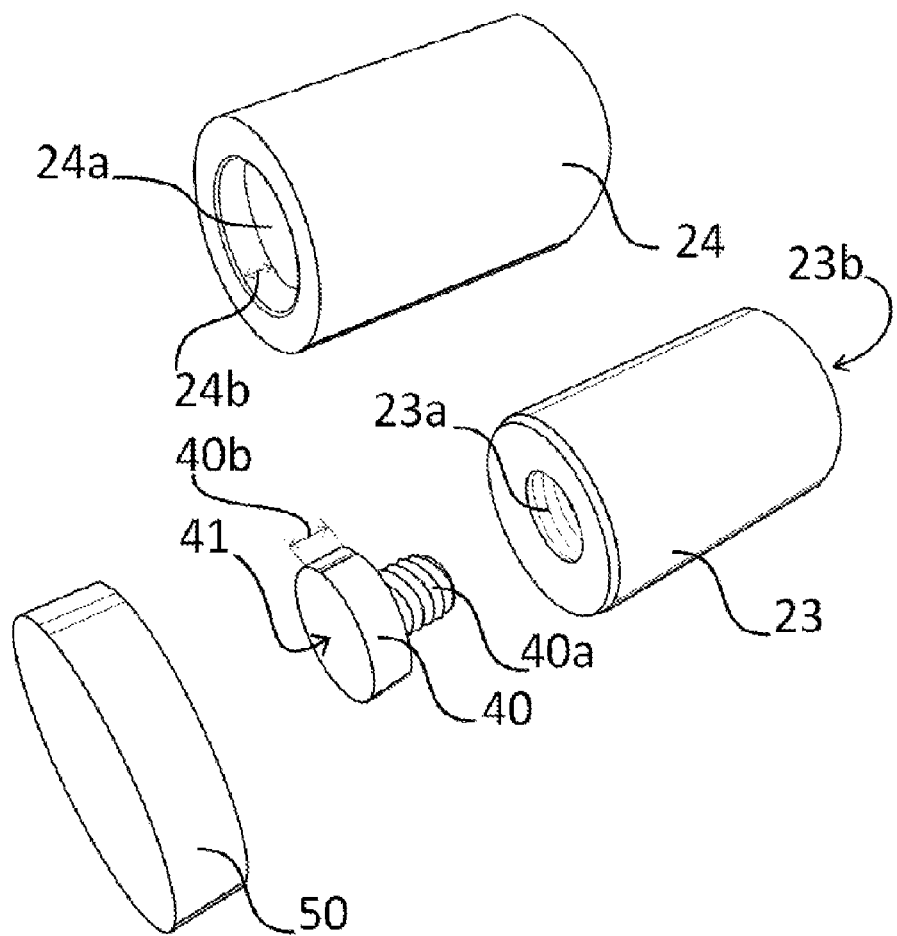
FIG. 1 illustrates a substrate, a standardised joining surface module, the mass body that can be screwed to the aforesaid, and a guide sleeve.

In the following Detailed Description, reference is made to the accompanying drawings, which form a part hereof, and in which is illustrated by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Against this background a device and a method for applying a directed contact pressure force to a multitude of samples while tolerating height differences in the individual samples are proposed. In one or more embodiments, according to a device and according to a method for simultaneously applying a predetermined identical pressure to a multitude of samples with the use of standardised joining surface modules, wherein a pressure exerted on the samples in a selected pressure region is independent of the sample height and independent of a selected ambient temperature or operating temperature.

In this context the term "sample" refers to:
the arrangement or the compound structure of a substrate, wherein the substrate includes an area intended for bonding, with an adhesive surface module, wherein the adhesive surface module includes an area intended for bonding, and an adhesive layer, arranged between the substrate and the adhesive surface module, or an adhesive reservoir arranged between the substrate and the adhesive surface module;
the arrangement or the compound structure of a substrate, wherein the substrate includes a contact area or connection area intended for soldering, with a solder surface module, wherein the solder surface module includes an area intended for soldering, and a solder, solder deposit or soldering paste arranged between the substrate and the solder surface of the solder surface module;
one of the above-mentioned arrangements or compound structures, wherein the respective module on the face pointing away from the substrate is additionally connected to a mass body that is used for first, temporary, fixing of the respective module.

For the sake of simplicity, the terms "adhesive surface module", "solder surface module" and "sample carrier", "test stamp" or "die stamp" are hereinafter represented by the term "joining surface module", irrespective as to whether the intended joined connection is an adhesive connection, a solder connection, a connection established by an intermetallic alloy, or some other integral connection that is associated with a phase transition or a phase change.

In this context the term "sample" relates to a not yet bonded, an already bonded, a not yet soldered, an already re-melted or soldered, or an otherwise integrally joined stack or to a stack destined for integral joining. Likewise, the term "sample" relates to an arrangement including a substrate, a respective means for the integral joining, or a joining means or a bonding agent and a joining surface module, wherein the joining surface module includes a first face that in the direction of the substrate is in contact with the joining means.

In this arrangement the substrate can, for example, be a solid body in the form of a material sample, selected from among a ceramic, a glass, a metal, a metallic alloy, a semiconductor, a laminate, a composite material, a mineral, a natural stone or an artificial stone, a mineral material, a crystal, a resin or a plastic material and in the form of a semi-finished product or in the form of a film or foil.

Because of the different material thicknesses of various substrates, their preceding surface treatment or coating with otherwise almost identical dimensions of the material samples, and/or because of the different thicknesses of layers of joining means, e.g., adhesive layers, adhesive deposits or solder deposits, even with the use of standardised joining surface modules of identical design and height, in each case different sample heights can result.

Further embodiments, modifications of and improvements to the proposed device and of/to the proposed method are stated in the following description and in the enclosed claims.

According to one embodiment, a device for applying a directed contact pressure force to a multitude of samples is proposed, wherein a first part of the device includes a multitude of receptacles adapted to receive in an ordered manner a multitude of adequately uniform samples, and a second part of the device is connectable to the first part in such a manner that a multitude of fluidically intercommunicating hydraulic cylinders in one of the two parts can load the joining surface modules simultaneously in a loading direction at a predetermined force that has been defined and is settable in respect to all the samples, which force is also essentially identical. This force is defined by the hydrostatic pressure achieved in hydraulic cylinders. The pressure or the respectively achievable pressure can be determined from a knowledge of the hydrostatic pressure and of the geometrically defined contact area between the substrate and the joining surface module and the number of the substrates/samples.

One or more advantages of this embodiment relate to the reliability of results obtained from samples that with the use of this device are to be subjected over a defined period of time to a defined force, if applicable as a force gradient. The proposed device is sufficiently compact for it to be able to simultaneously receive several samples, thus making it possible to obtain, in parallel, results from several samples of a different type but of similar geometry.

Such results relate, for example, to the strength of adhesive connections between a joining surface module and a sample, in one embodiment to the comparability of results obtained in this process concerning the reliability of adhesive connections or concerning their optimisation. A further advantage relates to an increase in the sample throughput. In order to safeguard comparability of test results from different test runs it is only necessary in each case to ensure identical hydrostatic pressure of the hydraulic fluid of the fluidically intercommunicating hydraulic cylinders. This is associated with further advantages with the use of adapted pressure control technology or adapted hydraulic fluids.

According to one embodiment, a device for applying a directed contact pressure force to a multitude of samples is proposed, wherein the first part and the second part are connectable or connected by using at least one holding element connected to the respective part. In this arrangement the respective holding elements comprise mutually corresponding forms, in other words the holding element of the first part includes a form that corresponds to the holding element of the second part, whereby the holding element of the second part also has a form that corresponds to that of the holding element of the first part.

This embodiment is associated with advantages in that it is possible to load samples easily and quickly into the device, to remove the samples easily and quickly from the device, and after completion of tests to easily disassemble the device. Any adhesive residues that may have issued from the sample stacks during testing and that may have cured can easily be removed because the receptacles of the joining surface module are easily accessible.

According to one embodiment, a device for applying a directed contact pressure force to a multitude of samples is proposed, wherein the first part of the device and the second part of the device are interconnectable by using holding elements of corresponding forms by way of a hinge, by way of a thread, by way of a bayonet coupling, by way of a plug-in rotary bolt, by way of a slot/slot-nut coupling or according to the key-lock principle.

This embodiment is associated with advantages in that it is possible to assemble the device easily and quickly, and to disassemble it just as easily after a test.

According to one embodiment, a device for applying a directed contact pressure force to a multitude of samples is proposed, wherein the receptacles at least in part are arranged at identical radial distance around the holding element.

This makes it possible to achieve a compact arrangement of numerous samples in a single device and increases the achievable sample throughput of each contact pressure process.

According to one embodiment, a device for applying a directed contact pressure force to a multitude of samples is proposed, wherein an external hydraulic drive can be connected to that part of the device, in which part the hydraulic cylinders are arranged, and consequently the hydraulic cylinders can be moved, by way of a shared hydraulic fluid reservoir, with an external hydraulic drive.

In this manner it is possible to exploit the advantages of a central test procedure. In one embodiment, with a separate hydraulic cylinder or an external hydraulic pressure device it is possible to achieve pressures in a hydraulic fluid, which pressures cannot without further ado be achieved by a central hydraulic fluid reservoir arranged directly in the device.

According to one embodiment, a device for applying a directed contact pressure force to a multitude of samples is proposed, wherein the device is adapted in such a manner that the hydraulic cylinders arranged in one of the two parts can jointly be subjected to hydrostatic pressure by using a hydraulic cylinder that is centrally arranged, so as to be movable, directly in the same part.

Advantages of this embodiment result from the possibility of a decentralised test procedure and from the elimination of additional external devices for operating the hydraulic cylinders. This embodiment is associated with a particular advantage in that the device is compact and not excessively heavy, so that in routine operation in a test laboratory it can still easily be transported and used, as required, by one person. Furthermore, the use of this device is tied to a laboratory. If applicable, the device can thus also be used in a mobile manner as required, and can be used on site.

According to one embodiment, a device for applying a directed contact pressure force to a multitude of samples is proposed, including a screw-type tensioning device that is adapted in such a manner that reproducible setting of the hydrostatic pressure and/or of the contact pressure force can take place. Advantageously, this makes possible the calibration of the device and the standardised manufacture of joined connections.

According to one embodiment, a device for applying a directed contact pressure force to a multitude of samples is proposed, wherein the screw-type tensioning device includes a marking or a dial, and the first part or the second part includes a marking or dial that corresponds to the marking or to the dial of the screw-type tensioning device, which latter marking is designed in such a manner that a discrete position of the screw-type tensioning device can reproducibly be set. This results in advantages to the standardised implementation of enquiries in the context of materials science, in one embodiment relating to the reproducibility of parameters set in this process.

According to one embodiment, a device for applying a directed contact pressure force to a multitude of samples is proposed, including a precision measuring screw or a micrometer screw, wherein the proposed screw-type tensioning device includes a precision measuring screw or a micrometer screw, and wherein the screw-type tensioning device includes a precision thread so that on a dial that is arranged parallel to an axis of the device the magnitude of an advance of the central hydraulic cylinder or of the tensioning device of the hydraulic cylinder can be read. In this arrangement the readable magnitude is typically readable in terms of the pitch of the screw thread of the screw-type tensioning device, typically expressed in whole or in half millimeters. A second dial along a circumference of the respective first or second part, including the screw-type tensioning device, of the proposed device is designed in such a manner that it is possible to read part of an entire pitch, which part only accounts for a fraction of a thread lead or of a pitch.

Advantages of this embodiment result from the measuring accuracy of a length or a travel of corresponding precision-mechanical precision measuring screws which are frequently also referred to as micrometer screws, precision measuring screws, or as precision-mechanical drives. In one embodiment, the precision measuring screw allows precise dosing of the pressure.

According to one embodiment, a device is proposed whose centrally arranged hydraulic cylinder includes a central pressure piston.

This is associated with an advantage in that the individual hydraulic cylinders, which fluidically communicate by way of the centrally arranged hydraulic cylinder, can be subjected to pressure by way of the aforementioned central pressure piston. Based on known physical conditions, the pressure exerted on the individual hydraulic cylinders by way of the hydraulic fluid is identical in respect to all the communicating hydraulic cylinders. However, differences from a preset pressure can occur when, as a result of an increase in the ambient temperature, the volume of the fluid (operating fluid) present in the hydraulic cylinder changes. In this arrangement the increased ambient temperature corresponds, for example, to a temperature for the correct processing of an adhesive (adhesive processing temperature) in an oven or in a climatic chamber. The adhesive processing temperature, which most of the time has been stated by the manufacturer, for example ensures curing or setting of the adhesive, and thus attaining an intended strength of the adhesive connection. Likewise, the increased ambient temperature can be selected in such a manner that it corresponds to the reflow temperature of a solder. Attaining the reflow temperature ensures complete wetting of the surfaces that are in contact with the solder deposit, and ensures a firm metallic connection between the solder and the joining surfaces. Overall, the proposed device makes it possible to achieve a standardised test procedure. The device improves the reliability of the results obtained.

According to one embodiment, a device is therefore proposed that furthermore includes at least one lever arm with a weight, wherein the weight exerts pressure on the central pressure piston by way of the lever effect.

This embodiment is, for example, associated with an advantage in that the force exerted on the central hydraulic cylinder can be set by selecting the lever (ratio of load arm to force arm) and the mass of the selected weight. It is understood that this device can be used independently of any external hydraulic pump, thus providing the device with almost unrestricted mobility. For example, the weight is suspended from the lever arm (load arm) or is affixed in some other location. This embodiment is associated with a significant advantage in that a force that is exerted, by way of the hydraulic cylinders in the central hydraulic cylinder or in the fluidically intercommunicating hydraulic cylinders, is independent of any volume increase of this fluid. It is thus possible to ensure that in regard to all the samples in the holding device the predetermined contact pressure force is independent of the temperature (ambient temperature) respectively set for correctly carrying out tests. As explained, the ambient temperature or the temperature of the device itself is set so that the joining means or bonding agent being investigated, for example an adhesive or a solder, develops the intended retention force or strength.

According to one embodiment, a device is proposed that includes two lever arms, wherein the two lever arms are arranged so as to be opposite each other so that in each case, by way of the lever effect, with a weight affixed to each lever arm they jointly exert pressure on the central pressure piston.

When compared to a device including only one lever arm, the aforementioned device is associated with an additional advantage in that, for example, it provides increased stability at identical or higher pressure, which pressure can be set by way of the mass of the weights.

According to one embodiment, a device is proposed wherein the weight includes partial weights or weight segments that can be affixed next to each other or to each other.

This embodiment of the weight provides an advantage in that depending on the respectively combined or respectively interconnected partial weights or weight segments a different pressure can be achieved, and in that different pressures can be achieved quickly. As an alternative, with the same objective it is also possible to affix different weights to different positions of the lever arm (load arm).

According to one embodiment, a device is proposed, wherein the overall mass of a weight affixed to the lever arm ranges between 1 kg and 10 kg, and individual partial weights or weight segments comprise masses of 100 g to 5 kg, masses of 500 g to 2 kg.

This is associated with an advantage in that a different pressure of the sample can be achieved step-by-step without elaborate refitting.

According to one embodiment, a device is proposed that furthermore includes a closable opening for filling the centrally arranged hydraulic cylinder with a fluid, wherein this opening can also be used for emptying the hydraulic cylinder. According to a variation of this embodiment, it is also possible for separate fill and discharge openings to be provided.

This is associated with an advantage in that it is possible to fill different operating fluids in the hydraulic system of the device without the need for elaborate refitting. These different fluids can advantageously be selected depending on the intended temperature range for measurements to be carried out.

According to one embodiment, a device for applying a directed contact pressure force to a multitude of samples is proposed, wherein a fluid situated in the hydraulic cylinder is not compressible and is stable at a temperature range preferable for curing the adhesive. Advantageously, this fluid is selected from water, an aqueous solution, a hydraulic oil, a silicone oil, a heat transfer fluid from the field of application of solar thermal technology. The resulting advantages relate to aspects of the reliability of the proposed device because a non-compressible fluid that is stable in the selected temperature range can be considered as a hydraulic fluid. Furthermore, for example, the easy availability, aspects of workplace health and safety, of environmental protection, as well as low costs are advantageous.

By way of the central hydraulic cylinder the applied pressure can evenly be transferred to the intercommunicating hydraulic cylinders of the individual contact pressure devices, wherein depending on the load applied to the samples the pressure which in each case rests on the areas of the substrate by way of the joining surface modules can easily be regulated and set in a targeted manner.

According to one embodiment, a device is proposed, wherein a clearance between a pressure point of a hydraulic cylinder and a contact pressure surface can be set or fixed by way of a locking nut. Advantages result from the usability of hydraulic cylinders with a short stroke, and thus an achievable small volume of the required hydraulic fluid, and from the resulting compact design of the device.

According to one embodiment, a device for applying a directed contact pressure force to a multitude of samples is proposed, which device furthermore includes a pressure display device for displaying a pressing force or a hydrostatic pressure. Advantages result from the usability of a pressure measuring head or of a sensor for automatic data acquisition and data storage, as well as from the possibility of measuring the pressure applied, or of controlling the pressure, if applicable by way of an additional feedback control system. For this purpose a central signal acquisition and signal processing unit can be provided.

According to one embodiment, a device for applying a directed contact pressure force to a multitude of samples is proposed, which device additionally includes a lock mechanism or a removable retention device that makes it possible to receive and/or transport the device in a tilt-free manner with an adapted retention means.

Since for application of the glue, for example, dosing devices or dosing stations are used, the retention device provided allows improved manageability and the transport of the device components loaded with glue(s) or with glues and samples from and to the dosing device or dosing station.

According to one embodiment, a device according to at least one of the preceding embodiments is proposed, which device furthermore includes at least one heating element for individually heating a joining surface module, received in a sample receptacle, and/or for heating a joining means that is in contact with the joining surface module, or for heating a joining means between the joining surface module in question and the substrate.

Advantages result in that different samples can be subjected to individually different temperatures or temperature gradients. Typically, the heating element is arranged in close proximity to the respective sample receptacle. It is thus possible, in relation to the sample in question, over a predetermined period of time to set an individual temperature of the sample.

According to one embodiment of the heating element, the heating element is selected from a resistance heater and an induction coil.

Advantages result in that the heat output of these heating elements can be precisely set and dosed. For example, with an induction coil, inductive heating can be achieved by using an eddy current. On the other hand, with a suitably controlled coil an adhesive including ferromagnetic particles can be selectively heated.

According to one embodiment, a method for simultaneously applying a predetermined pressure to a multitude of joining surface modules is proposed, wherein the pressure exerted on the samples is independent of the respective height of the samples, with the method including:

arranging the joining surface modules, which carry samples, in separate receptacles of a sample carrier in such a manner that in each case a first face of the joining surface module is aligned so as to be substantially parallel to the substrate;

connecting a cover plate with the sample carrier in such a manner that the cover plate in a first clearance to the sample carrier is aligned so as to be largely parallel to the sample carrier, wherein the first clearance is less than the average stroke of the hydraulic cylinders that are arranged either in the sample carrier underneath the samples, or in the cover plate frontally relative to the end faces of the samples;

simultaneously operating the hydraulic cylinders, and subjecting the samples to a predetermined pressure along or parallel to an axis that extends orthogonally to the plane defined by the sample carrier;

removing the samples.

The method is associated with advantages in that it is possible to use universal joining surface modules, for example joining surface modules including a threaded pin, in order to test the strength of a joined connection in an adapted test device under standard conditions, in each case relating to material pairings (samples) of interest in the form of a substrate that is integrally connected, with the use of a joining means, to a standardised joining surface module.

In this arrangement the connecting means can, for example, be selected from an adhesive, a glue, a cement, a solder, a metallic solder, a glass solder, a soldering paste or corresponding reservoirs which during curing, during setting, during reacting or during re-melting form an integral connection between a substrate and a first face of a joining surface module in the form of a cured adhesive or glue, of a set cement, of a re-melted solder or of an alloy with an intermetallic phase, of a polymer, of a resin or of other homogeneous or heterogeneous solid substances known to the average person skilled in the art.

The pin of the joining surface module, which pin has been inserted into a corresponding recess, for example a threaded hole of the mass body, ensures a stable position of the sample stack relative to a corresponding hydraulic cylinder of the second part of the device when the hydraulic cylinders are situated in the second part of the device.

Further advantages of this method relate, in one embodiment, to the comparability of results obtained, and findings derived, for example relating to the suitability of a glue, of a surface pre-treatment or of a dwell time, and to the increase in the sample throughput.

According to one embodiment, a method for simultaneously applying a predetermined pressure to a multitude of samples or sample stacks of different heights is proposed, which method furthermore involves applying at least one layer of a glue and at least one sample to a first face of a joining surface module.

This embodiment is associated with advantages in that at a given hydrostatic pressure of the hydraulic fluid, the pressure applied to the sample or to the sample stack is solely predetermined by the area of the (pin-) joining surface module, rather than by the height of the layer including the glue and the substrate as can be the case in known spring contact pressure devices.

According to one embodiment, a method for simultaneously applying a predetermined pressure to a multitude of samples of different heights is proposed, which method furthermore involves setting a predetermined temperature or a predetermined temperature gradient or temperature-controlling the device.

Advantages relate in one embodiment to thermosetting adhesives being able to be tested under defined conditions.

According to one embodiment, a method for simultaneously applying a predetermined pressure to a multitude of samples of different heights is proposed, wherein temperature-controlling takes place in the region from −40 to +500° C.

This embodiment is associated with advantages in one embodiment in that a comparison is possible of results that were obtained across a wide temperature range. Because, as a result of its robust design, the device can be manufactured entirely from metallic or high-temperature-resistant materials, the temperature resistance is only limited by the heat resistance or the thermal behaviour of the hydraulic fluid. This creates a wider scope of operation than is achievable by using conventional devices.

According to one embodiment of the proposed method, furthermore, temperature-controlling of at least one sample receptacle takes place, heating by using a heating element.

Advantages of this embodiment result from the possibility, in a sample holding device, to hold at different temperatures but in each case at identical pressure, identical material combinations, in each case including a layer of a joining means, for example an adhesive, applied to the joining surface of a joining surface module, and a substrate (or sample 50) that is in contact with the layer. This allows reliable comparison of the measurement values determined.

According to one embodiment of the method, the method involves individually measuring, by using an individual sensor, the temperature that is effectively achieved on a sample receptacle.

Advantages of this embodiment are due to the increased reliability of the measurement results and of the findings based thereon, and on the reproducibility of the tests.

The embodiments described above can be combined at will. In this process several embodiments can be selected and combined. Likewise, all the embodiments can be combined, while individual or several embodiments are left out or specific characteristics are left out.

The enclosed drawings illustrate embodiments and, together with the description, are used for clarifying the principles of the invention. The elements of the drawings are relative to each other and are not necessarily true to scale. Identical reference characters designate correspondingly similar components.

Device 1, 1a includes two parts 21, 22, wherein a first part 21, in the figures illustrated as the bottom part 21, is designed in the manner of a tray or plate that is used to receive a multitude of substrates 50, or to receive substrates 50 and samples and associated guide sleeves 24. The second part 22 covers the first part 21 at least in part in such a manner that centrally symmetrically opposite each sample receptacle 21a including a sample and a guide sleeve 24 a hydraulic cylinder 25 that runs in a fixed guide 31, or the pressure point 30 of the hydraulic cylinder 25 is arranged. Both parts 21, 22 are disconnectably interconnected.

FIG. 1 as an example illustrates the geometric conditions of a substrate 50, in the diagram designed as a disc, which substrate 50 can also be triangular, quadrangular or polygonal, which in each case, however, includes surfaces that are plane parallel relative to each other. Likewise, the substrate 50 can be a semi-finished product into which a smaller embodiment is to be pressed by using an adapted die stamp 40 (not illustrated in detail in the diagram), or which semi-finished product by using an adapted die stamp 40 (not illustrated in detail in the diagram) is to be embossed. In such a case it is possible to do without the plane parallelism by using suitable adapted receptacles 21a or inserts (not illustrated in the diagram) for the receptacles 21a.

According to one or more embodiments of the device, the first face 41 of a standardised joining surface module 40 is seated on one of the surfaces of the substrate. For temporarily fixing the standardised joining surface module 40 to a layer of a joining means, for example an adhesive, or a soldering paste deposit applied to one face of the substrate 50, the joining surface module can be screwed into a mass body 23. The mass body can be manufactured from a material of particularly high density, for example from a tungsten-copper compound or from a suitable heavy-metal alloy.

Typically the mass body for fixing the position of a guide sleeve 24 made to precisely fit is held exactly perpendicularly on the substrate surface that includes joining means. To this effect the mass body 23, before or after being screwed to the joining surface module 40, can be inserted in the guide sleeve 24 in such a manner that a front end of the mass body 23, which front end includes an internal thread 23a that matches the external thread 40a of the joining surface module 40, points to that face of the guide sleeve 24, which face includes a constricted passage opening 24a. The depth of the constriction of the constricted passage opening, or the wall thickness 24b of the constricted passage opening 24a, is adjusted to the height 40b of the joining surface module 40—without the pin including a thread—in such a manner that the first-mentioned is smaller than the last-mentioned. This results in a joining surface module placed on a substrate 50 being stabilised, prior to being pressed on, by using the device 1, 1a in a position that is precisely perpendicular to the substrate surface. This constriction thus acts as an abutment for the substrate/sample. The joining surface module itself can be inserted with appreciable play so that, for example, even in the case of adhesive leaking out, a situation is prevented where everything is bonded together.

Figure 2:
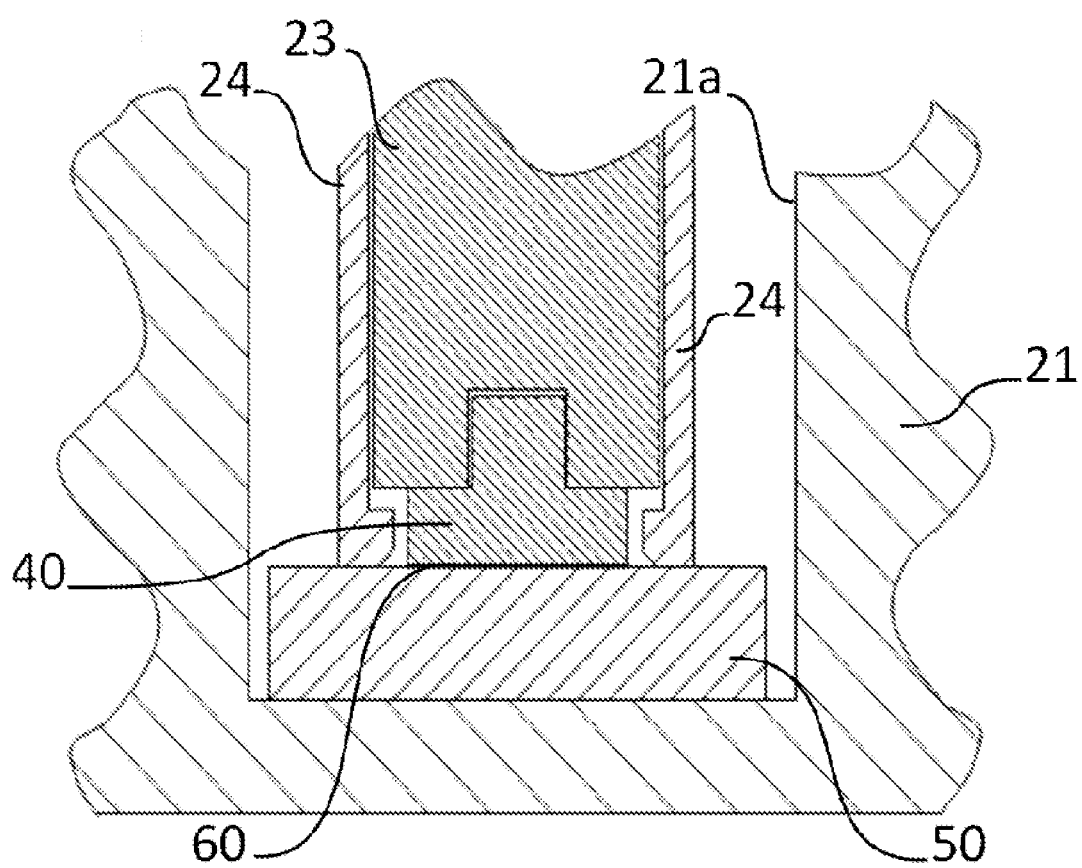
FIG. 2 illustrates a longitudinal section of part of a sample tray loaded with samples, which are to be joined or to be bonded, in guide sleeves.

FIG. 2 illustrates this in detail on the example of a first part 21 of the device 1, 1a, already in the receptacle 21a, which first part serves as a sample tray or bottom part.

In one embodiment, FIG. 2 illustrates the substrate 50 situated at the bottom of the receptacle 21a of the first part 21. The substrate includes a joining means, for example a glue.

According to exemplary embodiments, a first part 21 of the device 1, 1a, which first part at first is only loaded with substrates, by using a dosing device, a pipetting device or a printer head of a dosing station, pipetting station or printer station, can be provided with a predetermined quantity of the joining means 60—for example a soldering paste deposit, a solder ball deposit, a glue or a matrix of droplets of the components of a reactive adhesive mixture.

Likewise, the mass body 23, which fits precisely, runs freely in the guide sleeve 25, with the joining surface module 40 can be placed on a joining means 60. The guide sleeve 25 with its constricted passage opening 24a is seated directly on the bare substrate 50. In order to prevent any contact with the joining means 60, the diameter of the constricted passage opening 24a can be wider than the diameter of the joining surface module 40. As an alternative or in addition, an inner front rim of the constricted passage opening can be bevelled or rounded.

Figure 3:
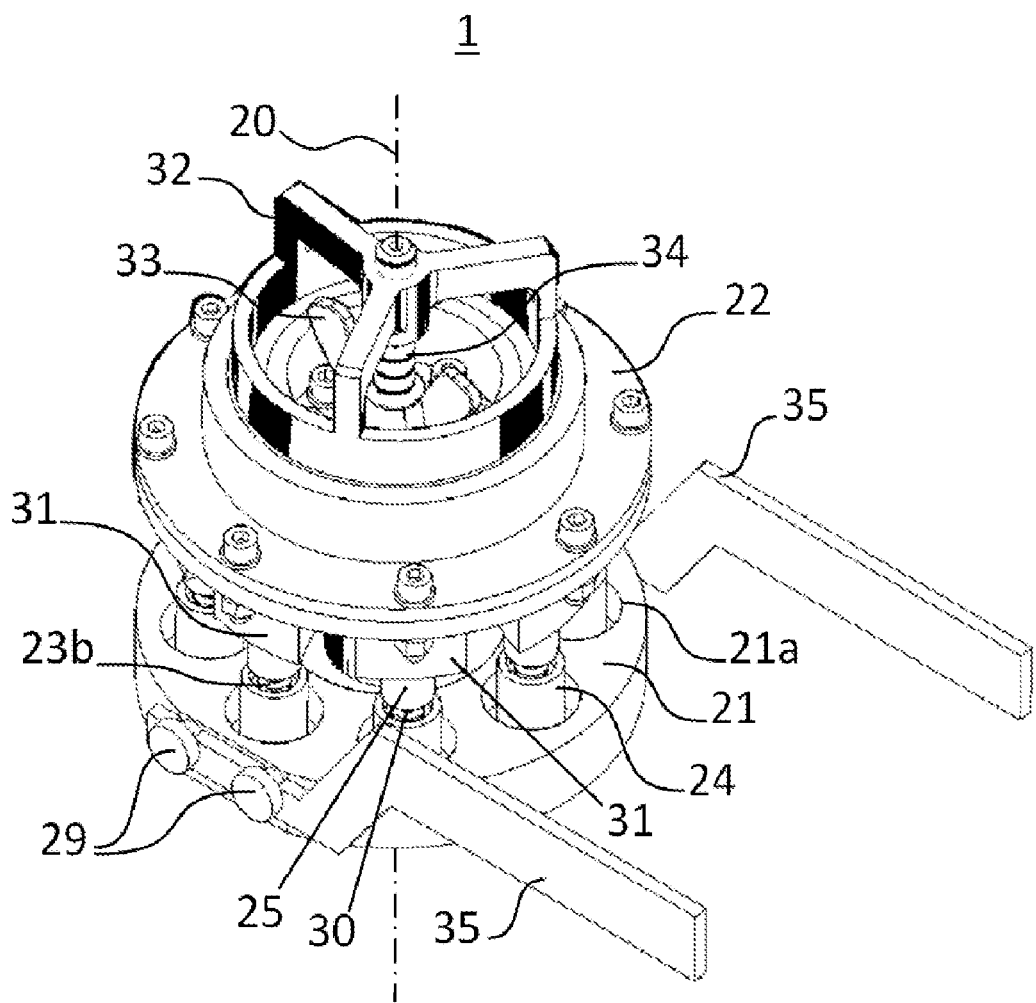
FIG. 3 illustrates an embodiment of the proposed device that is adapted for receiving by using removable gripper arms.

FIG. 3 illustrates one exemplary embodiment 1 of the device with locking means 29 or retention means 29 that are arranged so as to be symmetrical to an axis 20, with the device in its assembled state. In this arrangement the receptacles 21a of the bottom or first part 21 of the device 1, which bottom or first part 21 serves as a sample tray, are loaded with samples stabilised by guide sleeves 24. Visible in the guide sleeves are the contact pressure surfaces 23b of the mass body 23, which contact pressure surfaces 23b point in the direction of the contact pressure points 30 of hydraulic cylinders 25. Each of the hydraulic cylinders 31 typically includes a hydraulic cylinder 25, which runs in a fixed guide 31, with a central pressure point 30, wherein in FIG. 3 only the external contour of the contact pressure point 30 is visible.

A screw-type wing nut 33, which can be screwed onto a central threaded rod 34, is designed to lower and lock the second part 22 of the device 1, 1a near the sample surface in front of the highest sample in the bottom first part 21 of the device.

The hydrostatic pressure in a central fluid reservoir of the device 1 or its central hydraulic cylinder (covered up), which central fluid reservoir is fluidically connected to all the hydraulic cylinders 25 including pressure points 30, can be regulated and reproducibly set by using a tensioning device 32 screwably arranged on a central axis 20 on an internal thread of the second or top part 22 of the device.

Figure 4:
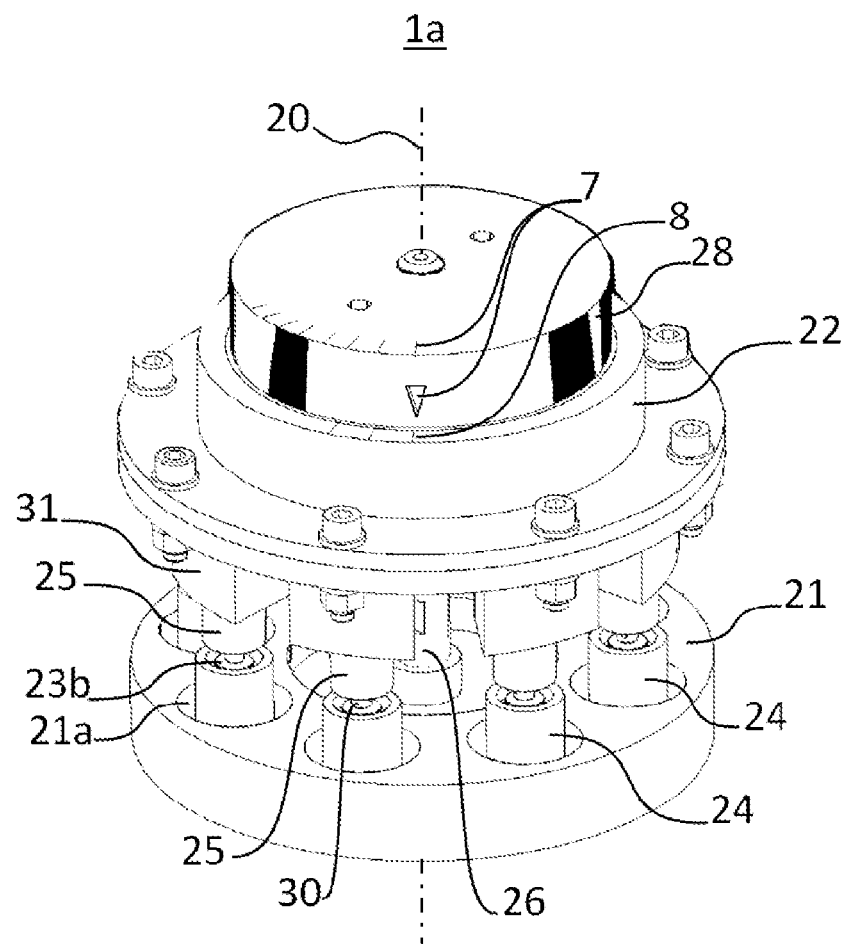
FIG. 4 illustrates an embodiment of the device with a dial display.

FIG. 4 illustrates an alternative embodiment 1a of the device with a screw-type tensioning device 28 that includes a marking 7. The marking can be implemented in various ways. The position of the marking relative to a circumferential dial on the second part 22 is used to set the hydrostatic pressure or to calibrate the pressing force. The dial, which circumferentially revolves by 360 degrees, or a graduation and the marking can jointly be used for reproducibly setting a pressure.

Figure 5:
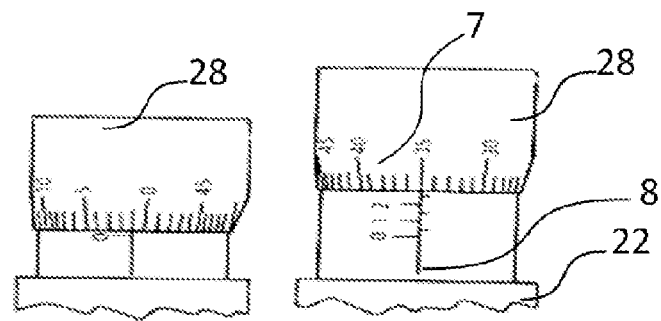
FIG. 5 illustrates a section of an embodiment with a tensioning device in the form of a precision measuring screw or micrometer screw.

As an alternative, the respectively completed mechanical advance of the central hydraulic cylinder can be used, by a tensioning device 28 in the form of a precision adjustment screw or micrometer screw including a precision thread and a ratchet, for calibrating the built-up hydrostatic pressure or the pressing force achieved on the sample. Such an embodiment with different advance of the central hydraulic cylinder is diagrammatically illustrated in FIG. 5. Dials that correspond to each other can simultaneously be vertically readable, vertically and horizontally readable, or horizontally readable, so that both dials can be read at a glance from above onto the device. As an alternative, the arrangement and design of the dials can make it possible to read the dial graduation or associated dial values both horizontally and vertically. Variants of these embodiments are illustrated, as examples, in FIGS. 4 and 5.

Figure 6:
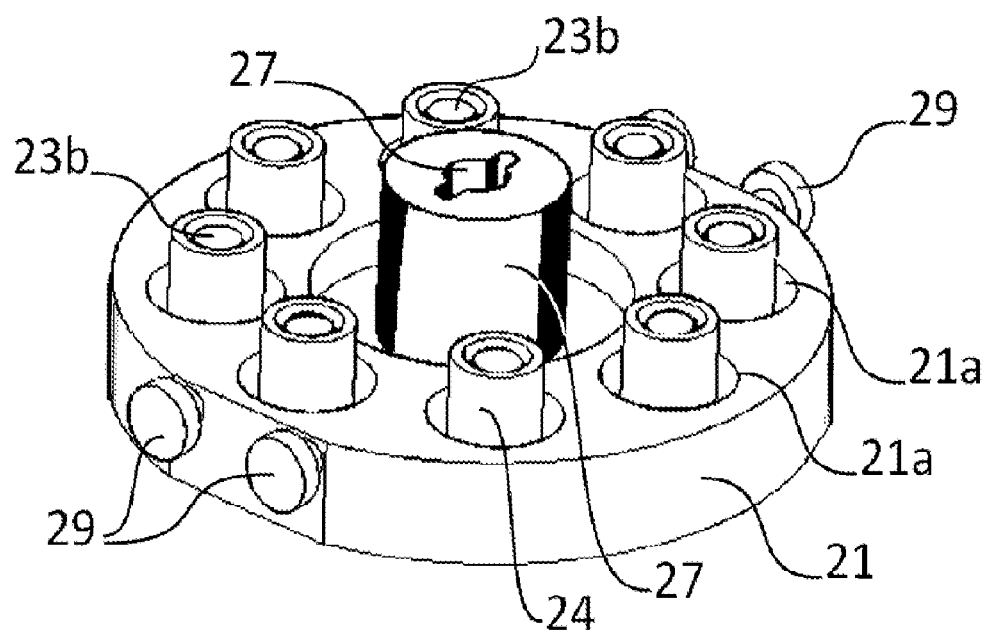
FIG. 6 illustrates a first part of the device, designed as a sample tray, which first part in corresponding receptacles is loaded with samples in guide sleeves.

FIG. 6 illustrates a detailed view of the first part 21 of the device 1 with eight receptacles 21a concentrically arranged on a connecting element 26. Each receptacle 21a includes a sample. The contact pressure surfaces 23b of the mass bodies 23 are supported by the guide sleeves. Laterally, locking mechanism or means 29 or retention means 29 are provided that make possible facilitated holding of the device with a suitable gripper arm. By using a gripper 35 the device loaded with samples can, if applicable, be automatically transported in a tilt-free manner.

The connecting element is designed in the form of a bayonet coupling 27. The corresponding counterpiece of the bayonet coupling is situated on the second part 22 of the device 1.

Figure 7:
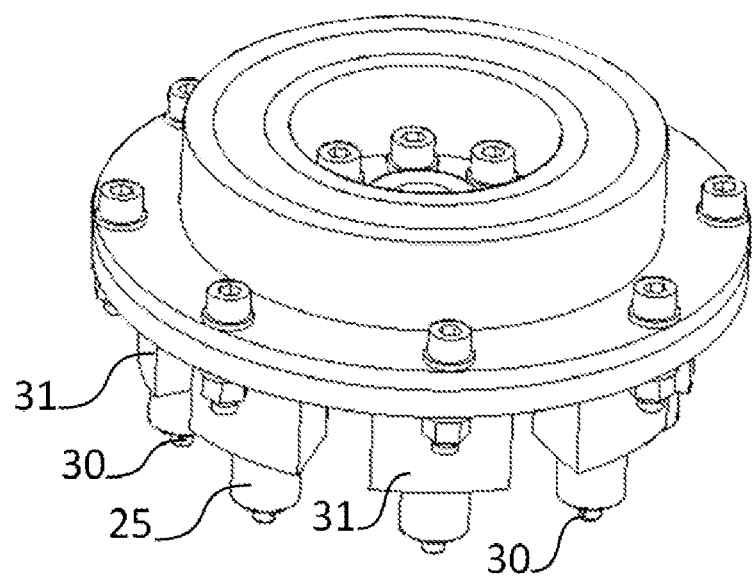
FIG. 7 illustrates an embodiment of the part of the device including hydraulic cylinders and a central hydraulic cylinder (not visible) with the contact pressure mechanism having been removed.

FIG. 7 illustrates the second or top part of the device, including fluidically intercommunicating hydraulic cylinders 25, in each case running in a fixed guide 31 and including pressure points 30 centrally arranged on the aforesaid.

Figure 8:
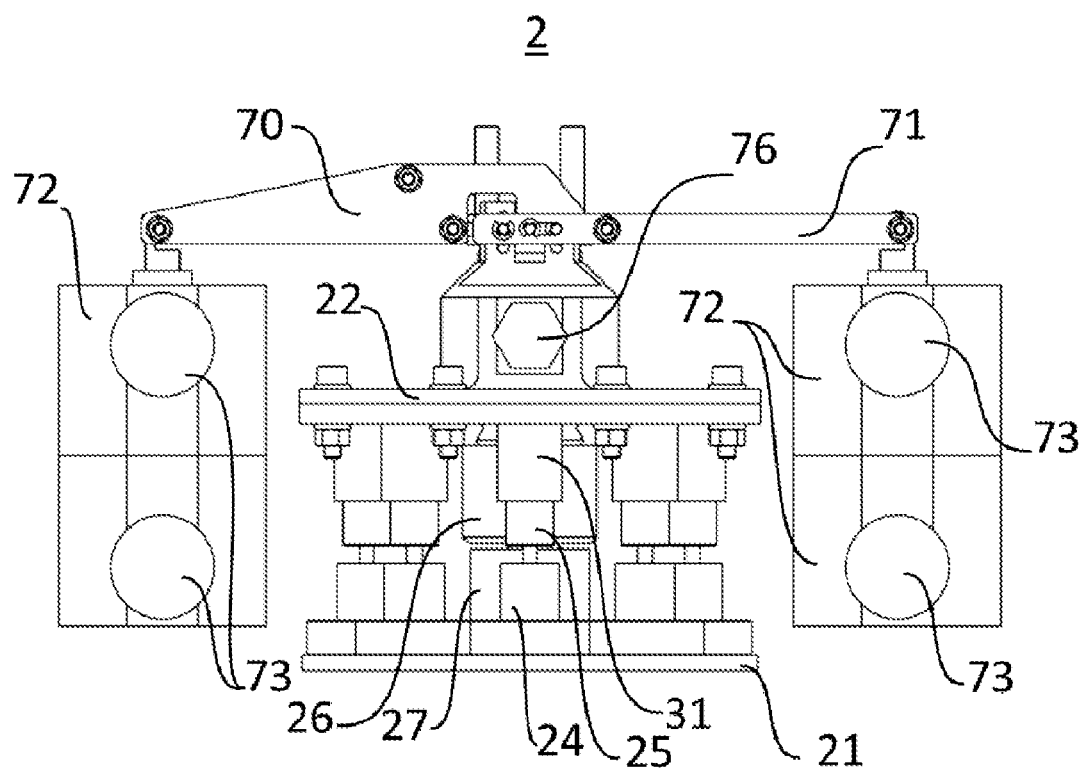
FIG. 8 illustrates a front view of an embodiment of the device with a lever mechanism for compensating for volumetric changes in a hydraulic operating medium during heating.

FIG. 8 illustrates the front view of a further embodiment 2 of the device with two cooperating levers 70, 71. The force exerted on the samples by the individual hydraulic cylinders 25 is thus independent of the respective temperature of the external surroundings, which temperature in each case corresponds to an operating temperature set in a targeted manner.

The temperature set (ambient temperature), for example in a laboratory oven or in a heating chamber, corresponds, for example, to a processing temperature of a hot-curing adhesive (adhesive processing temperature). Typical adhesive processing temperatures range, for example, from 80° C. to 250° C. In one embodiment, the processing temperature of a hot-melt adhesive (physically curing adhesive) can be at a temperature of around 200° C. Likewise, a chemically-curing adhesive can be cured by the addition of heat.

During the individual heating of individual or all the material pairings "joining surface module//joining means//substrate" situated in the respective sample receptacles, in addition in each case an individual temperature can be set. In one embodiment, electrically operated heating elements are suitable for such individual heating. Such a heating element can be based on the principle of a resistance heater/Joule heat, or on the principle of inductive heating. Likewise, by using electromagnetic alternating fields an adhesive layer can be selectively heated if the layer includes magnetic particles. Suitable glues comprise, for example, nanoparticles whose diameter is smaller than the intended layer thickness of the glue. While a typical thickness of an adhesive surface of 10 to 500 µm, in one embodiment to 400 µm, is typically 100 to 200 µm, the particles have a diameter of approximately 10 to 15 nm. Typically a ferromagnetic core of the particles is at least 10 nm in size.

In one embodiment, metallic nanoparticles of iron, cobalt or alloys based thereon can be considered as fillers of joining means that can be heated in this manner. Advantageously, in this arrangement an adhesive layer can be selectively heated without a substrate that is in contact with the adhesive being subjected excessively to thermal loads. Usually the adhesive filled in such a manner is heated by an external magnetic field that is coupled in by way of a coil arranged in or underneath the sample receptacle. By way of the frequency, if applicable the pulse rate, voltage and current, it is possible to very precisely set a defined temperature in the adhesive layer, and the adhesive applied can be cured "from the inside".

An ambient temperature around 200° C. results in a distinct expansion of the operating fluid used in the hydraulic system. For example, the resulting pressure can differ from an intended and preset pressure if the expansion of the operating fluid (hydraulic fluid) or of the container has not been taken into account.

The device which, as described, includes at least one lever arm is associated with a particular advantage in that the pressure, which has been pre-set by way of a selected weight or partial weights and by way of the length of the lever arm, is in fact held and maintained irrespective of the ambient temperature during the test procedure (joining, e.g., gluing, soldering). Falsification of a pre-set pressure as a result of expansion of the operating fluid used in a hydraulic cylinder or a change, as a result of expansion, in the size of an operating cylinder is thus prevented. This facilitates the standardised test procedure and improves the reliability of results obtained. In the receptacles, which are provided for this purpose, of the lower part/sample tray 21 the samples (not specially designated in the diagram) are arranged. Thereafter the first or bottom part 21 of the device 2 is connected to the second or top part 22 of the device 2 by way of centrally arranged connecting elements 26, 27. The hydraulic system is filled with a suitable fluid. To this effect an operating fluid, e.g., a hydraulic oil, which is adapted to the test temperature or the respectively set ambient temperature, is filled into the hydraulic system, by way of an opening (not illustrated) that is closed by way of a fill or discharge screw, in a manner that prevents bubbles from arising. After this, the device can be arranged in a climatic chamber or in an oven, where the desired temperature is being set or has already been set.

Figure 9:
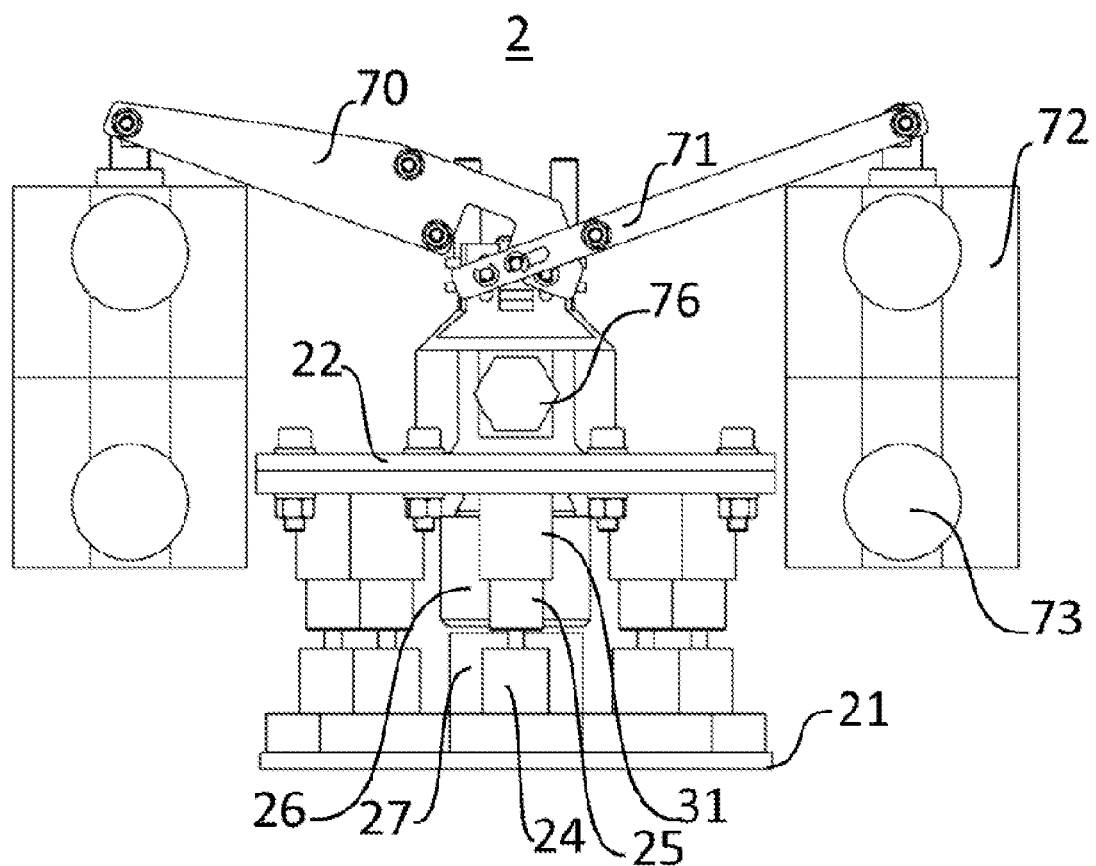
FIG. 9 illustrates the front view of the embodiment of the device with a lever mechanism for compensating for volumetric changes of a hydraulic operating medium during heating in the lifted state, i.e., in a volume of the operating fluid in the hydraulic system of the sample holding device, which volume has been increased as a result of expansion (the representation is slightly exaggerated).

FIG. 9 illustrates the front view of this embodiment of the device. In the diagram, the lever mechanism is illustrated in its raised state. The weights are lifted because of the expansion, resulting from the temperature, of the operating fluid in the hydraulic system. When the hydraulic operating fluid expands as a result of an increase in the ambient temperature, without this lever mechanism this would manifest itself in a force that is excessive proportional to the volume increase and that differs from the preset value. This in turn can result in a reduced thickness of an adhesive layer of the samples tested. If no such lever device is used, the pressure attained under real test conditions at an ambient temperature of 200° C. can significantly differ from the value, which has been pre-set by using a knurled-head screw, as a result of thermal effects (expansion of the hydraulic fluid, volumetric change of the device). A temperature of 200° C. definitely corresponds to an exemplary processing temperature relating to particular high-temperature adhesives or to a reflow soldering temperature of particular solder pastes or solder deposits.

The described lever mechanism 70, 71 makes it possible to do without the use of the previously described measuring screw or tensioning device 28. By using a lever device that exerts pressure on a central work cylinder, the multi-sample press-on device can be used at ambient temperatures that correspond to the processing temperature of high-temperature adhesives or of solders. The pressure that in each case is achieved in the hydraulic system, and thus the pressing force occurring on the sample, is independent of an almost unavoidable expansion of the operating fluid used in the hydraulic system.

Figure 10:
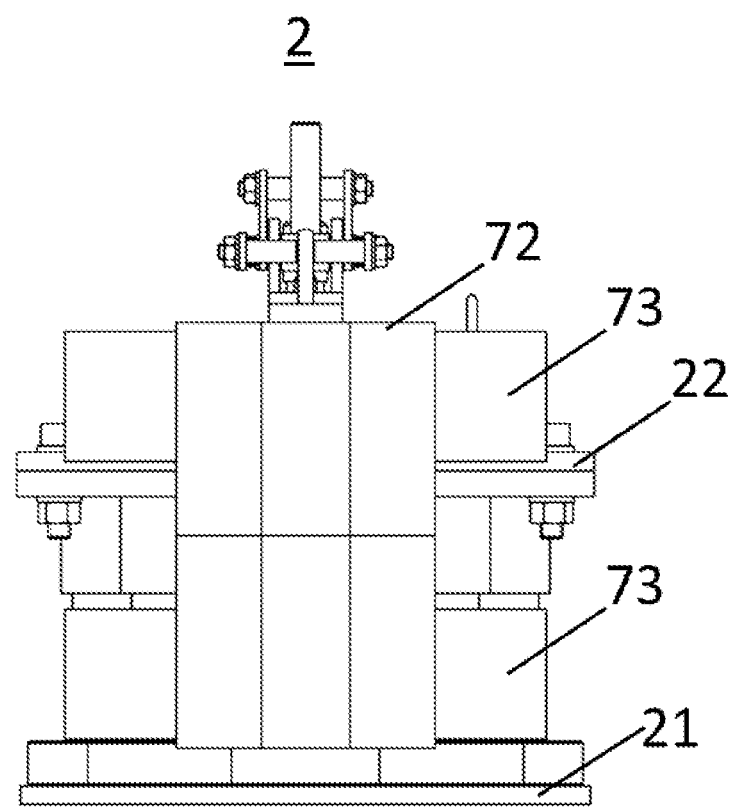
FIG. 10 illustrates a lateral view of the embodiment according to FIG. 8.

FIG. 10 illustrates a lateral view of the embodiment 2 of the device with a lever mechanism. The partial weights 73, which have been attached to the weights 72, do not laterally protrude beyond the width of the top part 22 or bottom part 21. In this diagram, too, the compact form of the proposed design is evident.

Figure 11:
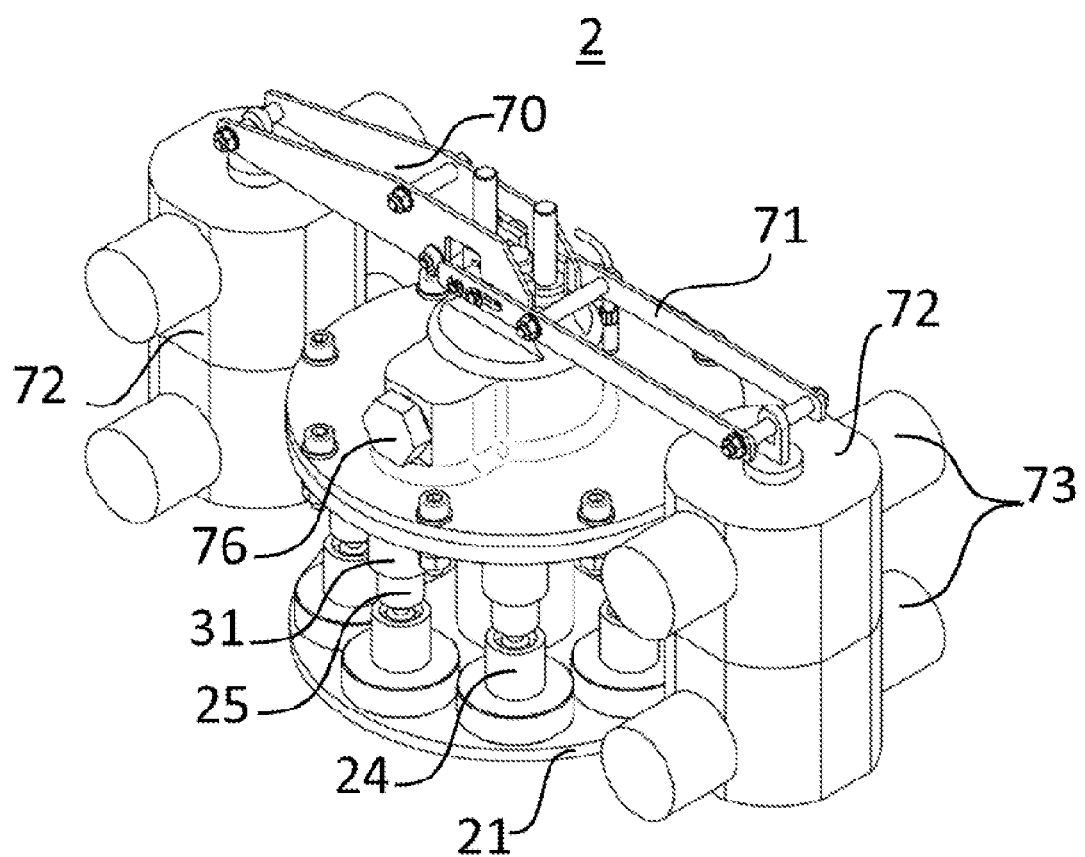
FIG. 11 illustrates a perspective front view of this embodiment.
Figure 12:
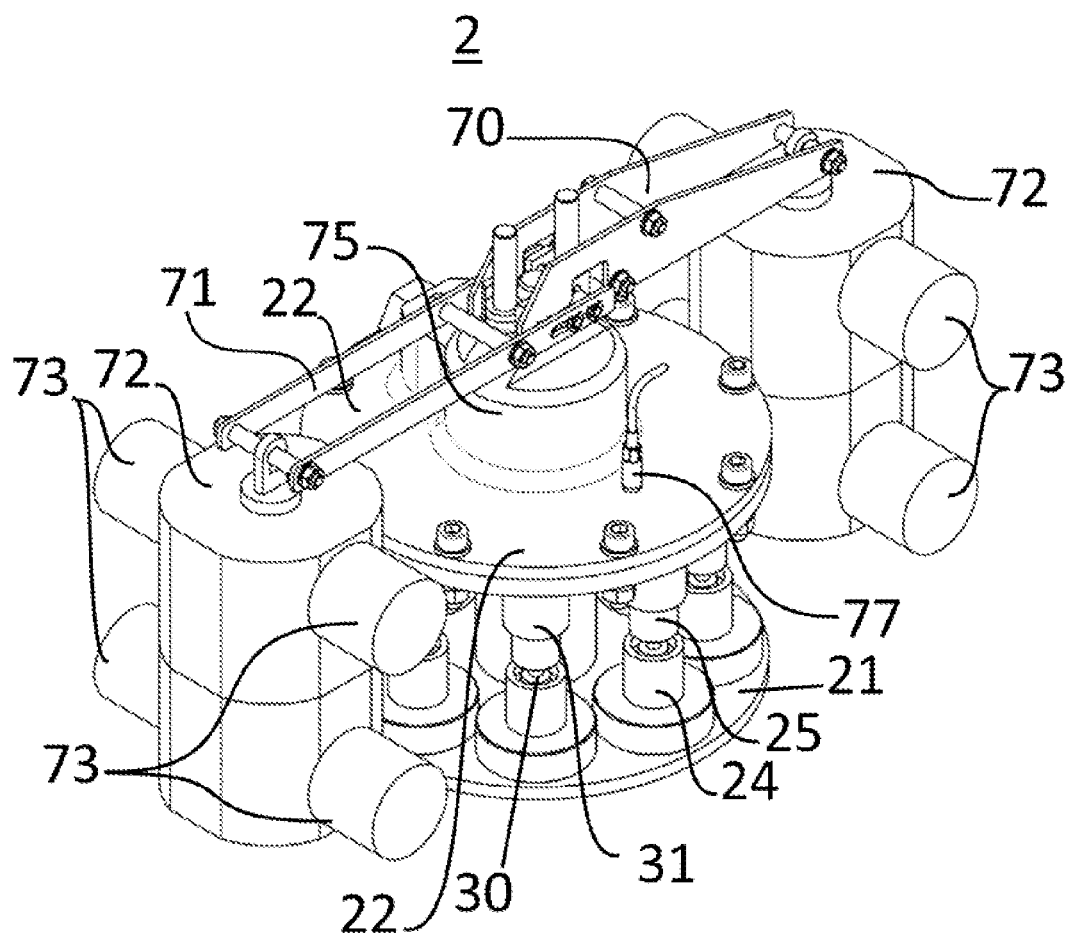
FIG. 12 illustrates a perspective view of the rear of this embodiment.

FIGS. 11 and 12 illustrate perspective views of one embodiment of the device 2 with a double lever mechanism, respectively from the front and from the rear. In this design the two lever arms 70, 71 are constructed from two interconnected parts. In the embodiment illustrated, the two lever arms engage each other and, in each case by way of a bearing, exert pressure on a central pressure piston or on the central hydraulic cylinder 75. Other embodiments, for example including only one lever arm, are also possible. A separately affixed measuring probe 77 can be used for the real-time acquisition of the pressure present in the hydraulic system. Further probes, for example a temperature probe, a thermocouple or a pressure load cell, can be integrated in the device in a suitable manner.

FIGS. 11 and 12 illustrate the arrangement of the weights 72, 73, which have been constructed from elements that are easy to interconnect. Depending on the partial weights 72 or weight segments 73 that are respectively to be combined, or that are respectively combined, a different pressure can be achieved. As an alternative, with the same objective it is also possible to attach various weights at different positions of the lever arm (load arm).

For example, the overall mass of a weight attached to the lever arm can range from 1 kg to 10 kg and can be composed of individual partial weights 72, 73 or weight segments of a mass of 100 g to 5 kg. For example, a partial weight 72, 73 suspended from the lever arm can comprise a mass of 500 g to 2 kg. In one or more embodiments, the weights that in each case are attached to the lever arm can be divisible and in addition can be lightened by laterally arranged segments (round pieces) 73, so that, for example, a variation of the mass of between 2 kg; 2.5 kg; 4 kg; 4.5 kg and 5 kg on each side can be achieved. Correspondingly, approximately 40 to 100% of the maximum pressure force achievable with the respective lever arm is exerted. The weights can, for example, be made from brass.

According to preferred embodiments, the connection between a first and a second part is implemented by way of at least one holding element 26, 27 that can be arranged centrally along an imaginary axis 20. A mechanical-hydraulic contact pressure mechanism includes individually extendable hydraulic cylinders 25 that in each case run in a fixed guide 31 arranged parallel to the imaginary axis 20. The number and arrangement of the hydraulic cylinders corresponds to the number and arrangement of the receptacles in the first part of the device, thus determining the number of samples that can be handled in a pressing process.

The use of the device makes it possible, for example, to improve the reproducibility of customary methods for testing the strength of adhesive connections, in that the pressure exerted on each sample is independent of the respective height of the sample or of the layer design including the joining surface module/adhesive layer/substrate.

According to one embodiment of a method, for example, first the pin of a joining surface module 40, which pin includes a thread 40a, is affixed in the mass body 23 and is placed onto the substrate including the joining means to be tested. Depending on the nature and constitution of the joining means used, for example of an adhesive, the aforesaid can take place immediately after application of the joining means or after a period of time has passed.

Following the above, the second part of the device is lowered, as closely as possible to the sample surface, to just above the highest sample and is locked. To this effect it is possible for either complete lowering of the second part 22 or, in the case of an axially-fixed second part, for merely lowering of the hydraulic contact pressure mechanism of the second part to take place. The contact pressure mechanism itself includes a central hydraulic fluid reservoir that feeds individual, smaller, hydraulic cylinders. After the entire contact pressure mechanism has been lowered to near the surface of the sample, the contact pressure mechanism, if applicable with the aid of a guide or guides, is then also locked towards the top, and parallel to this or following this, the pressure in the central hydraulic fluid reservoir is increased, which results in further extension of the individual hydraulic cylinders downwards in the direction of the sample.

In this manner the hydraulic cylinders, depending on the sample height, gradually establish contact with the samples. After all the hydraulic cylinders are in contact with the samples, the samples are subjected to uniform contact pressure. The adhesion pressure can then be increased in a defined manner, by a further increase in the pressure in the central hydraulic fluid reservoir, simultaneously in respect to all the samples, irrespective of any different sample heights, until the desired set value has been reached.

The described device and the proposed method are more reliable when compared to hitherto-known solutions. The hitherto commonly applied placement of a mass body in the form of a metal plate results in comparable pressures only in respect to samples of identical sample heights. The latter is, however, indispensable for the provision of uniform adhesive thickness and consequently of curing behaviour, which is uniform from one sample to another, of the adhesive, and this again is a prerequisite for bonding strength that is uniform from one sample to another. Samples with typical diameters in the centimeter range or below can be connected, i.e., bonded or otherwise joined either integrally or having positive fit, simultaneously with identical pressure, wherein in terms of sample height neither microscopic height tolerances nor certain macroscopic differences (manufacturing-related differences in the sample heights) result in any limitations relating to reproducibility.

The proposed device and the proposed method are associated with a significant advantage in that in each case simultaneously several samples of differing heights can be subjected to pressure that is identical in respect to all the samples. In this process the pressure can be reproducibly set and is thus defined and determinable according to suitable calibration methods.

Furthermore, by combining suitable modules, adapted mass bodies and matching guide sleeves, with the proposed device or with the method based thereon, a situation is achieved in which the first face of the joining surface module is arranged so as to be plane-parallel to the substrate surface, wherein the gap between the joining surface module and the substrate is and remains completely filled with the joining means because the position of the components of the sample is stabilised during the actual joining process. Thus in respect to all the samples pressed with the proposed device, even if the samples differ in height, identical pressure is ensured while maintaining their alignment relative to each other. The device and the method are suitable for various applications in the field of joining technology, in one embodiment for integral joining, and also for stamping, die stamping and pressing.

Embodiments of the device or the proposed method can be used whenever parallel subjection of a multitude of object identical pressure or contact force is required, for example for applications in materials testing relating to adhesives technology, in strength testing or in other field of materials research and quality management.

Combinations of the above-mentioned embodiments make it possible to provide a device and its application according to a standardisable concept, in one embodiment of a test procedure. On the one hand, the standardisability is based on the defined pressing force, which is identical in respect to all the samples to be joined, irrespective of their height. On the other hand, advantageous combinations of the embodiments described make it possible to simultaneously process several samples in one joining process, and to increase the sample throughput.

Although in this document specific embodiments have been presented and described, it is within the scope of the present invention to suitably modify the embodiments illustrated, without leaving the scope of protection of the present invention. The following claims represent a first, non-binding, attempt to generally define the invention.

What is claimed is:

1. A device for applying a directed contact pressure force to a multitude of samples comprising:
   a first part comprising a multitude of sample receptacles adapted to receive a multitude of joining surface modules of the same kind;
   a second part of the device is connectable to the first part in such a manner that a multitude of fluidically intercommunicating hydraulic cylinders in one of the two parts can load the joining surface modules simultaneously in a loading direction at a predetermined force that is substantially identical in respect to all samples;
   wherein the hydraulic cylinders arranged in one of the parts are configured such that they can jointly be subjected to hydrostatic pressure by using a hydraulic cylinder that is centrally arranged, so as to be movable, directly in the same part;
   wherein the centrally arranged hydraulic cylinder comprises a central pressure piston; and
   further comprising a lever arm with a weight that exerts pressure on the central pressure piston by way of the lever effect.

2. The device according to claim 1, wherein the first part and the second part are connectable or connected by using at least one holding element connected to each respective part, and wherein a first holding element of the first part comprises a form that corresponds to a second holding element of the second part.

3. The device according to claim 1, wherein the first part is connected to the second part by using holding elements of corresponding forms by way of a hinge, by way of a thread, by way of a bayonet coupling, by way of a plug-in rotary bolt, by way of a slot/slot-nut coupling or according to the key-lock principle.

4. The device according to claim 1, wherein the sample receptacles are arranged at substantially identical radial distance around the holding element.

5. The device according to claim 1, wherein the weight comprises partial weights or segments that are affixed next to each other.

6. The device according to claim 1, wherein the weight has an overall mass ranging between 1 and 10 kg, and individual partial weights or weight segments comprise masses of 100 g to 5 kg, masses of 500 g to 2 kg.

7. The device according to claim 1, further comprising a closable opening for filling the centrally arranged hydraulic cylinder with a fluid and/or for discharging a fluid.

8. The device according to claim 1, wherein a fluid situated in the hydraulic cylinders is a fluid that is not compressible and is stable at a selected temperature range, with the fluid being selected from: water, an aqueous solution, a hydraulic oil, a silicone oil, and a heat transfer fluid from the field of application of solar thermal technology.

9. The device according to claim 1, wherein a clearance between a pressure point of the fluidically intercommunicating hydraulic cylinders and a contact pressure surface can be set and/or fixed by way of a locking nut.

10. The device according to claim 1, further comprising a display device for displaying a pressing force or a hydrostatic pressure.

11. The device according to claim 1, additionally comprising:
    a lock mechanism for the tilt-free receiving and/or transport of the device with a retention means.

12. The device according to claim 1, wherein at least one sample receptacle comprises a heating element for individually heating the joining surface module, received in the sample receptacle, and/or for heating a joining mechanism that is in contact with the joining surface module.

13. The device according to claim 12, wherein the at least one heating element is selected from a resistance heater and an induction coil.

14. A device for applying a directed contact pressure force to a multitude of samples comprising:
    a first part comprising a multitude of sample receptacles adapted to receive a multitude of joining surface modules of the same kind;
    a second part of the device is connectable to the first part in such a manner that a multitude of fluidically intercommunicating hydraulic cylinders in one of the two parts can load the joining surface modules simultaneously in a loading direction at a predetermined force that is substantially identical in respect to all samples;
    wherein the hydraulic cylinders arranged in one of the parts are configured such that they can jointly be subjected to hydrostatic pressure by using a hydraulic cylinder that is centrally arranged, so as to be movable, directly in the same part;
    wherein the centrally arranged hydraulic cylinder comprises a central pressure piston; and
    wherein two lever arms are arranged so as to be opposite each other so that in each case, by way of the lever effect, with a weight they exert pressure on the central pressure piston.

* * * * *